United States Patent [19]
White

[11] Patent Number: 4,595,773
[45] Date of Patent: Jun. 17, 1986

[54] METHOD FOR PREPARING COPPER-DIAMINE COMPLEXES AND DIAMINES

[75] Inventor: Dwain M. White, Schenectady, N.Y.

[73] Assignee: General Electric Company, Schenectady, N.Y.

[21] Appl. No.: 694,571

[22] Filed: Jan. 24, 1985

[51] Int. Cl.$^4$ .................. C07F 1/08; C07C 61/12; C07C 61/28; C07C 63/33
[52] U.S. Cl. ........................... 556/110; 556/114; 564/492; 564/498
[58] Field of Search .............. 260/438.1, 429 J; 564/498, 492; 556/110, 114

[56] References Cited

U.S. PATENT DOCUMENTS

| | | | |
|---|---|---|---|
| 2,686,798 | 8/1954 | Gmitter | 260/438.1 X |
| 2,924,551 | 2/1960 | Harwood et al. | 260/438.1 X |
| 2,924,552 | 2/1960 | Harwood et al. | 260/438.1 X |
| 2,928,856 | 3/1960 | Harwood et al. | 260/438.1 |
| 2,943,100 | 6/1960 | Holstein | 260/429 J |
| 2,977,279 | 3/1961 | Kosmin | 260/438.1 X |
| 3,036,104 | 5/1962 | Matzinger | 260/429 J |
| 3,914,266 | 10/1975 | Hay | 260/438.1 |
| 3,980,654 | 9/1976 | Gysling | 260/438.1 X |
| 4,160,785 | 7/1979 | Webb et al. | |

OTHER PUBLICATIONS

Basolo et al, JACS, 76, 211–214 (1954).

*Primary Examiner*—Helen M. S. Sneed
*Attorney, Agent, or Firm*—William H. Pittman; James C. Davis, Jr.; James Magee, Jr.

[57] ABSTRACT

Copper-diamine complexes such as copper(II)-di-t-butylethylenediamine dibromide are prepared by the reaction of a dihalide such as 1,2-dibromoethane with an amine such as t-butylamine and a basic copper(II) compound such as cupric oxide in a nitrile solvent. The diamine can be liberated from the complex by reacting it with a complexing agent such as an ethylenediaminetetraacetic acid salt.

19 Claims, No Drawings

METHOD FOR PREPARING COPPER-DIAMINE COMPLEXES AND DIAMINES

This invention relates to the preparation of copper-diamine complexes and the corresponding diamines. More particularly, it relates to a method for preparing diamines in high yields and with a minimum of by-products, wherein a copper-diamine complex is obtained as an intermediate.

Various diamines in which both nitrogen atoms are secondary or tertiary are useful as components of catalyst systems used to prepare polyphenylene oxides (also known as polyphenylene ethers) by the oxidative coupling of phenols. Among the diamines useful for this purpose as N,N'-di-t-butylethylenediamine (hereinafter DBEDA) and N,N'-diphenylethylenediamine. The polyphenylene oxides produced by the use of these catalysts are in wide use as constituents of engineering resins.

A method commonly used for the preparation of DBEDA and similar diamines is by the reaction of a primary amine such as t-butylamine with a dihaloalkane such as 1,2-dibromoethane. Another method, disclosed in U.S. Pat. No. 4,160,785, is the hydrogenation of a diimine formed by the reaction of a dialdehyde such as glyoxal with a primary amine such as t-butylamine. Both of these reactions form, in addition to the desired product, a number of by-products such as N,N'-di-t-butylpiperazine, N,N'-di-t-butylimidazolidine, t-butylaziridine and vinyl bromide. Many of these by-products are toxic, some are suspected carcinogens, and none display catalytic activity in the oxidative coupling reaction. Therefore, there is continued interested in developing methods of synthesizing such diamines.

U.S. Pat. No. 3,914,266 describes the reaction of diamines of this type with cupric bromide to produce copper-diamine complexes which are also useful as catalyst constituents for polyphenylene oxide preparation. In order to obtain the complexes by this method, of course, it is necessary first to prepare the diamine by one of the above-described methods. Thus, the preparation of the complexes is subject to the same disadvantages as the preparation of the diamines themselves.

A principal object of the present invention, therefore, is to provide a new synthetic method for preparing copper-diamine complexes and the corresponding diamines.

A further object is to provide a method for preparing the diamines using the copper-diamine complexes as intermediates.

A further object is to provide a preparation method which affords the desired product in high yields and with a minimum of by-products.

A still further method is to provide a new method for preparing materials useful as catalyst constituents in the oxidative coupling of phenols to polyphenylene oxides.

Other objects will in part be obvious and will in part appear hereinafter.

In one of its aspects, the present invention is a method for preparing a copper-diamine complex having the formula

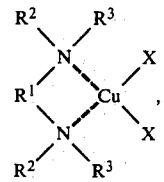

wherein:

$R^1$ is an ethylene, trimethylene or $C_{5-6}$ 1,2- or 1,3-cycloalkylene radical which, if substituted, contains only phenyl substituents or tertiary alkyl substituents containing about 4–8 carbon atoms;

$R^2$ is an alkyl radical containing up to about 8 carbon atoms or a phenyl radical;

$R^3$ is hydrogen, an alkyl radical containing up to about 8 carbon atoms or a phenyl radical; and X is chlorine, bromine or iodine;

said method comprising reacting a dihalide of the formula $R^1X_2$ with an amine of the formula $R^2NHR^3$ and at least one basic copper(II) compound in at least one aliphatic or aromatic nitrile as diluent.

The dihalide used in the method of this invention may be a dichloride, dibromide or diiodide, or a mixed dihalide such as a chlorobromide. The $R^1$ value therein may be an ethylene, trimethylene or 1,2- or 1,3-cyclopentylene or cyclohexylene radical, or a corresponding phenyl- or t-alkyl-substituted radical such as phenylethylene, diphenylethylene, t-butylethylene, (3-methyl-3-pentyl)ethylene, (2,4,4-trimethyl-2-pentyl)ethylene or 3-t-butyl-1,3-cyclohexylene. Preferably, the $R^1$ radical contains at most one substituent, and more preferably it is unsubstituted. The ethylene radical is especially preferred.

The amine may be primary or secondary and is usually primary. The $R^2$ value therein may be phenyl or an alkyl radical such as methyl, 1-propyl, 2-propyl, 1-butyl, 2-butyl, t-butyl or 2,4,4-trimethyl-2-pentyl. The t-alkyl radicals and especially t-butyl are preferred. The $R^3$ value is usually hydrogen but may be any of the radicals listed for $R^2$. Thus, suitable amines include dimethylamine, diethylamine, 1-propylamine, 2-propylamine, t-butylamine, 1-pentylmethylamine and 1-octylamine, with t-butylamine being particularly preferred because of its availability and the high utility of the diamine thus produced as a catalyst constituent.

Illustrative basic copper(II) compounds which may be used in the method of this invention are cupric oxide, cupric sulfide, basic cupric acetate and basic cupric carbonate. It is strongly preferred that the copper compound be halide-free. Because of its availability and relatively low cost, cupric oxide is the preferred basic copper compound.

The rate of reaction of the basic copper(II) compound depends to some extent on the proportion of available surface area thereon. It is therefore preferred to use it in a form which has a high surface area. An example is "copper oxide wire", commercially available from Fisher Scientific Company.

Another essential feature of the method of this invention is the diluent, which is at least one aliphatic or aromatic nitrile such as acetonitrile, propionitrile, butyronitrile or benzonitrile. The saturated aliphatic nitriles and especially acetonitrile are preferred. Mixtures of nitriles may be used but their use seldom provides any benefit.

The method of this invention is typically conducted by heating a mixture of the four above-described materials at a temperature typically in the range of about 50°–120° C., and preferably about 70°–100° C., until the reaction is complete. Mixtures of this type are another aspect of the invention. When the diluent is acetonitrile, the reaction may be conveniently conducted at reflux since the boiling point of acetonitrile is about 82° C. The progress of the reaction can be visually followed by the disappearance of the basic copper(II) compound as it is consumed. When consumption thereof has ceased, the reaction may be considered to have proceeded as far as possible.

Isolation of the copper-diamine complex may be effected by crystallization from the reaction mixture by evaporating and/or cooling. If desired, the complex may be further purified by recrystallization or the like, but such further purification is generally unnecessary.

It will be apparent from formula I that the reaction theoretically involves two moles of amine, one mole of dihalide and an amount of basic copper compound containing one gram-atom of copper. In practice, it is often advantageous to employ a slight excess of amine, typically about 2.1–2.5 moles per mole of dihalide. The reaction mixture typically comprises about 40–60% reactants, with the balance being diluent.

As is apparent from formula I, the diamine ligand in the copper complex has the formula

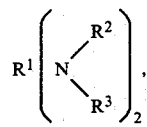
(II)

wherein $R^1$, $R^2$ and $R^3$ are as previously defined. This diamine may be liberated from the complex by reacting it with a stronger complexing agent for copper(II) than the diamine, and this reaction constitutes another aspect of the present invention.

Suitable complexing agents for preparation of the diamine include, in general, all compounds which complex more strongly with copper than the diamine. Such compounds include ammonium ion, cyanide ion, and chelating agents such as ethylenediaminetetraacetic acid and its salts and nitrilotriacetic acid and its salts. The salts of ethylenediaminetetraacetic acid, especially the alkali metal salts and most desirably the trisodium salt, are preferred. It is generally convenient to use an excess of complexing agent, typically in solution in water and/or a relatively polar organic diluent. The liberated diamine may then be isolated and purified by conventional techniques.

The invention is illustrated by the following examples. All parts, percentages and proportions are by weight.

EXAMPLE 1

A mixture of 1.60 parts (20 mmol.) of cupric oxide wire, 3.5 parts (48 mmol.) of t-butylamine, 3.76 parts (20 mmol.) of 1,2-dibromoethane and 10.7 parts of acetonitrile was heated to reflux under nitrogen, with vigorous stirring. Heating and stirring were continued for 20 hours, at which time all the cupric oxide had dissolved and an orange-brown precipitate had formed. The mixture was cooled to 25° C., whereupon additional solid precipitated. It was removed by filtration, washed with acetonitrile and dried under vacuum. There was obtained 2.0 grams of a product which was shown to be the copper(II)-DBEDA bromide complex by comparison with an authentic sample. Further complex was obtained by evaporation of acetonitrile from the filtrate.

EXAMPLE 2

The copper(II)-DBEDA bromide complex prepared in Example 1 was added to an excess of a 10% solution of trisodium ethylenediaminetetraacetate in a water-ether mixture. The mixture was stirred until the solids disappeared. After separation from the aqueous layer, the organic phase was analyzed by gas chromatography and shown to comprise DBEDA and N,N'-di-t-butylimidazolidine in a ratio of 99:1. The DBEDA was isolated by evaporation of the ether.

Similar treatment of the solid obtained in Example 1 by the evaporation of the acetonitrile yielded a product shown by analysis to contain DBEDA, N,N'-di-t-butylimidazolidine and N,N'-di-t-butylpiperazine in a ratio of 90:5:3.

EXAMPLE 3

The procedure of Example 1 was repeated, substituting benzonitrile for the acetonitrile and conducting the reaction at 85° C. When cupric oxide dissolution had ceased, the mixture was filtered; analysis of the residue showed that 94% of the cupric oxide had been consumed. Upon isolation of the complex and treatment with trisodium ethylenediaminetetraacetate as in Example 2, a product was obtained which was shown by nuclear magnetic resonance spectroscopy to be DBEDA.

What is claimed is:

1. A method for preparing a copper-diamine complex having the formula

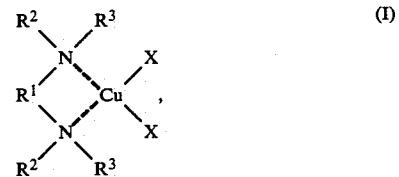
(I)

wherein:
$R^1$ is an ethylene, trimethylene or $C_{5-6}$ 1,2- or 1,3-cycloalkylene radical which, if substituted, contains only phenyl substituents or tertiary alkyl substituents containing about 4–8 carbon atoms;
$R^2$ is an alkyl radical containing up to about 8 carbon atoms or a phenyl radical;
$R^3$ is hydrogen, an alkyl radical containing up to about 8 carbon atoms or a phenyl radical; and
X is chlorine, bromine or iodine;
said method comprising reacting, at a temperature in the range of about 50°–120° C., a dihalide of the formula $R^1X_2$ with an amine of the formula $R^2NHR^3$ and at least one basic copper(II) compound in at least one aliphatic or aromatic nitrile as diluent; about 2.1–2.5 moles of amine and an amount of basic copper compound containing 1 gram-atom of copper being used per mole of dihalide.

2. A method according to claim 1 wherein the nitrile is acetonitrile.

3. A method according to claim 2 wherein the basic copper(II) compound is cupric oxide.

4. A method according to claim 3 wherein X is bromine.

5. A method according to claim 4 wherein $R^1$ is the ethylene radical.

6. A method according to claim 5 wherein $R^2$ is t-butyl or phenyl and $R^3$ is hydrogen.

7. A method according to claim 6 wherein $R^2$ is t-butyl.

8. A method according to claim 6 wherein the reaction is conducted at a temperature within the range of about 50°–120° C.

9. A method according to claim 8 wherein $R^2$ is t-butyl.

10. A mixture comprising a dihalide of the formula $R^1X_2$, an amine of the formula $R^2NHR^3$, at least one basic copper(II) compound and at least one aliphatic or aromatic nitrile; wherein:
   $R^1$ is an ethylene, trimethylene or $C_{5-6}$ 1,2- or 1,3-cycloalkylene radical which, if substituted, contains only phenyl substituents or tertiary alkyl substituents containing about 4–8 carbon atoms;
   $R^2$ is an alkyl radical containing up to about 8 carbon atoms or a phenyl radical;
   $R^3$ is hydrogen, an alkyl radical containing up to about 8 carbon atoms or a phenyl radical; and
   X is chlorine, bromine or iodine.

11. A composition according to claim 10 wherein the basic copper(II) compound is cupric oxide and the nitrile is acetonitrile.

12. A composition according to claim 11 wherein X is bromine.

13. A composition according to claim 12 wherein $R^1$ is the ethylene radical.

14. A composition according to claim 13 wherein $R^2$ is t-butyl and $R^3$ is hydrogen.

15. A method for preparing a diamine of the formula

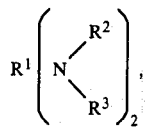
(II)

wherein:
   $R^1$ is an ethylene, trimethylene or $C_{5-6}$ 1,2- or 1,3-cycloalkylene radical which, if substituted, contains only phenyl substituents or tertiary alkyl substituents containing about 4–8 carbon atoms;
   $R^2$ is an alkyl radical containing up to about 8 carbon atoms or a phenyl radical; and
   $R^3$ is hydrogen, an alkyl radical containing up to about 8 carbon atoms or a phenyl radical;
which comprises reacting a copper-diamine complex of the formula

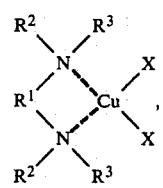
(I)

wherein X is chlorine, bromine, or iodine, with a complexing agent selected from the group consisting of ammonium ion, cyanide ion, ethylenediaminetetraacetic acid and its salts and nitrilotriacetic acid and its salts.

16. A method according to claim 15 wherein X is bromine and $R^1$ is the ethylene radical.

17. A method according to claim 16 wherein the complexing agent is a salt of ethylenediaminetetraacetic acid.

18. A method according to claim 17 wherein $R^2$ is t-butyl and $R^3$ is hydrogen.

19. A method according to claim 18 wherein the complexing agent is trisodium ethylenediaminetetraacetate.

* * * * *